(12) United States Patent
Shapiro

(10) Patent No.: US 12,271,350 B2
(45) Date of Patent: *Apr. 8, 2025

(54) SYSTEM AND METHOD OF JOINING RESEARCH STUDIES TO EXTRACT ANALYTICAL INSIGHTS FOR ENABLING CROSS-STUDY ANALYSIS

(71) Applicant: Josh Shapiro, Smyrna, GA (US)

(72) Inventor: Josh Shapiro, Smyrna, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/742,044

(22) Filed: Jun. 13, 2024

(65) Prior Publication Data
US 2024/0330251 A1 Oct. 3, 2024

Related U.S. Application Data

(63) Continuation of application No. 17/887,127, filed on Aug. 12, 2022, now Pat. No. 12,019,593.

(51) Int. Cl.
*G06F 16/21* (2019.01)

(52) U.S. Cl.
CPC .................. *G06F 16/211* (2019.01)

(58) Field of Classification Search
CPC .............................. G06F 16/211; G16H 10/20
See application file for complete search history.

(56) References Cited

U.S. PATENT DOCUMENTS

| | | | | |
|---|---|---|---|---|
| 8,484,254 B1 * | 7/2013 | Rock | ...................... | G16H 10/20 707/804 |
| 11,586,524 B1 * | 2/2023 | Jain | ..................... | G06F 11/3438 |
| 2003/0061096 A1 * | 3/2003 | Gallivan | ................ | G06Q 30/02 705/14.66 |
| 2009/0138251 A1 * | 5/2009 | Bugrim | .................. | G16B 50/20 703/11 |
| 2011/0029439 A1 * | 2/2011 | Castillo | ................ | G06Q 10/101 705/300 |
| 2014/0058782 A1 * | 2/2014 | Graves, Jr. | ............. | G06Q 10/06 702/179 |
| 2019/0318810 A1 * | 10/2019 | Gkoulalas-Divanis | ...................... | G06F 21/6227 |
| 2019/0378621 A1 * | 12/2019 | Ellison | .................... | G06F 3/011 |
| 2020/0250562 A1 * | 8/2020 | Bly | ...................... | G06F 16/9024 |
| 2021/0191908 A1 * | 6/2021 | Lott | ....................... | G06N 20/00 |
| 2021/0265025 A1 * | 8/2021 | Katnani | ................. | G06Q 50/22 |
| 2023/0060252 A1 * | 3/2023 | Bly | ....................... | G06F 18/285 |

* cited by examiner

*Primary Examiner* — Jorge A Casanova
(74) *Attorney, Agent, or Firm* — Boris Leschinsky

(57) ABSTRACT

A processor-implemented method and a system for user-selected selected joining two or more research studies to extract analytical insights for enabling cross-study analysis is disclosed. The method includes identifying, using an identification module, at least one matched variable in a statistically representative sample in each of the two or more research studies. The method further includes establishing, using a segment establishing module, for each combination of matched variables, a schema of segments, from the two or more research studies. The method furthermore includes determining, using the segment establishing module if each of the established schema of segments is statistically representative. The method furthermore includes creating a joint study, using a joint study creation module, by combining responses from each of the two or more research studies within each segment of the statistically representative schema of segments.

12 Claims, 14 Drawing Sheets

|   | INDEX2 | Dataset1 | Dataset2 |
|---|---|---|---|
| 1 | F-Advanced | 0.110 | 0.10555556 |
| 2 | F-Basic | 0.128 | 0.13888889 |
| 3 | F-Intermediate | 0.052 | 0.06888889 |
| 4 | F-Less than B | 0.124 | 0.12222222 |
| 5 | M-Advanced | 0.122 | 0.14222222 |
| 6 | M-Basic | 0.238 | 0.21333333 |
| 7 | M-Intermediate | 0.074 | 0.08111111 |
| 8 | M-Less than B | 0.152 | 0.12777778 |

FIG. 2A

| A | B | C | D |
|---|---|---|---|
| Gender | Education | Proportion in the sample | Proportion in the population |
| Male | Less than ba | 21% | 15% |
| Male | Basic | 8% | 6% |
| Male | Intermediate | 8% | 13% |
| Male | Advanced | 13% | 17% |
| Female | Less than ba | 13% | 18% |
| Female | Basic | 8% | 13% |
| Female | Intermediate | 10% | 6% |
| Female | Advanced | 19% | 14% |

FIG. 2C

| A | B | C | D |
|---|---|---|---|
| Gender | Education | Proportion in the sample | Proportion in the population |
| Male | Less than ba | 21% | 15% |
| Male | Basic | 8% | 6% |
| Male | Intermediate | 8% | 13% |
| Male | Advanced | 13% | 17% |
| Female | Less than ba | 13% | 18% |
| Female | Basic | 8% | 13% |
| Female | Intermediate | 10% | 6% |
| Female | Advanced | 19% | 14% |

FIG. 2D

| Index3 | Dataset1 | Dataset2 |
|---|---|---|
| F-Advanced-[20-25] | 16 | 24 |
| F-Advanced-[26-30] | 16 | 32 |
| F-Advanced-[31-35] | 8 | 14 |
| F-Advanced-[35-40] | 10 | 21 |
| F-Advanced-[41-45] | 5 | 4 |
| F-Basic-[20-25] | 12 | 35 |
| F-Basic-[26-30] | 24 | 39 |
| F-Basic-[31-35] | 12 | 20 |
| F-Basic-[35-40] | 12 | 28 |
| F-Basic-[41-45] | 4 | 3 |
| F-Intermediate-[20-25] | 6 | 19 |
| F-Intermediate-[26-30] | 9 | 24 |
| F-Intermediate-[31-35] | 4 | 6 |
| F-Intermediate-[35-40] | 6 | 11 |
| F-Intermediate-[41-45] | 1 | 2 |
| F-Less than B-[20-25] | 13 | 37 |
| F-Less than B-[26-30] | 20 | 32 |
| F-Less than B-[31-35] | 9 | 17 |
| F-Less than B-[35-40] | 16 | 18 |
| F-Less than B-[41-45] | 4 | 6 |
| M-Advanced-[20-25] | 18 | 29 |
| M-Advanced-[26-30] | 23 | 36 |
| M-Advanced-[31-35] | 9 | 26 |

FIG. 2E

|  |  |  |
|---|---|---|
| Male | Less than basic | Rejected |
| Male | Basic | Not Rejected |
| Male | Intermediate | Not Rejected |
| Male | Advanced | Rejected |
| Female | Less than basic | Not Rejected |
| Female | Basic | Not Rejected |
| Female | Intermediate | Not Rejected |
| Female | Advanced | Not Rejected |

FIG. 2F

| | |
|---|---|
| F-Advanced-[20-25] | Not Rejected |
| F-Advanced-[26-30] | Not Rejected |
| F-Advanced-[31-35] | Not Rejected |
| F-Advanced-[36-40] | Not Rejected |
| F-Advanced-[41-45] | Not Rejected |
| F-Basic-[20-25] | Not Rejected |
| F-Basic-[26-30] | Not Rejected |
| F-Basic-[31-35] | Not Rejected |
| F-Basic-[36-40] | Not Rejected |
| F-Basic-[41-45] | Not Rejected |
| F-Intermediate-[20-25] | Not Rejected |
| F-Intermediate-[26-30] | Rejected |
| F-Intermediate-[31-35] | Not Rejected |
| F-Intermediate-[36-40] | Not Rejected |
| F-Intermediate-[41-45] | Not Rejected |
| F-Less than B-[20-25] | Rejected |
| F-Less than B-[26-30] | Not Rejected |
| F-Less than B-[31-35] | Not Rejected |
| F-Less than B-[36-40] | Not Rejected |
| F-Less than B-[41-45] | Not Rejected |
| M-Advanced-[20-25] | Not Rejected |
| M-Advanced-[26-30] | Rejected |
| M-Advanced-[31-35] | Not Rejected |
| M-Advanced-[36-40] | Not Rejected |

|  | 'gender', 'age' | 'gender', 'educ' | 'age', 'educ' | 'gender', 'age', 'educ' |
|---|---|---|---|---|
| Number of Segments Created | 6 | 8 | 12 | 24 |
| Number of Segments Created |  |  |  |  |
| Sample Size Test: % of Segments that Passed | 100 | 100 | 100 | 100 |
| Proportions Test: % of Segments that Passed, Average P-Value | 100%, P-value = 1 | 100%, P-value = 1 | 100%, P-value = 1 | 100%, P-value = 1 |
| Average p-value for means test (1 var) | 0.5 | 0.69 | 0.52 | 0.61 |

400

|  | 'gender', 'age' | 'gender', 'educ' | 'age', 'educ' | 'gender', 'age', 'educ' |
|---|---|---|---|---|
| Number of Segments Created | 6 | 8 | 12 | 24 |
| Number of Segments Created |  |  |  |  |
| Sample Size Test: % of Segments that Passed | 100% | 100% | 100% | (df1: 0.92, df2: 0.58) |
| Proportions Test: % of Segments that Passed, Average P-Value | 100%, 0.73 | 100% 0.73 | 100% 0.76 | 100% 0.6 |
| Average p-value for means test (1 var) | 0.42 | 0.4 | 0.76 | 0.6 |
| Means |  |  |  |  |

SYSTEM AND METHOD OF JOINING RESEARCH STUDIES TO EXTRACT ANALYTICAL INSIGHTS FOR ENABLING CROSS-STUDY ANALYSIS

CROSS-REFERENCE TO RELATED APPLICATIONS

This application is a continuing application and claims a priority benefit from a co-pending U.S. patent application Ser. No. 17/887,127 filed on 12th August 2022, now U.S. Pat. No. 12,019,593, which in turn claims priority to U.S. provisional patent application No. 63/232,734, filed on 13th August 2021, the complete disclosure of these applications, in their respective entireties, is herein incorporated by reference.

BACKGROUND

Technical Field

The embodiments herein generally relate to statistical data analysis, and more particularly, to processor-implemented method and system of joining two or more studies to extract analytical insights for enabling cross-study analysis.

Description of the Related Art

Currently, a research study typically contains statistical, exploratory, or other analysis within a specific data set that is collected. Examples of research studies include surveys, market research, social science experiments, polling data or other in-field collected research, and the like. Typically, if a researcher intends to combine insights from two or more research studies, then the researcher needs to re-run the data collection and ask questions from both (or all) studies, and subsequently analyze the combined study. Currently, researchers have two approaches for combining research studies including: 1) Meta-analysis and 2) Comparative analysis. Meta-analysis allows researchers to combine the findings of multiple research studies and summarize the insights. For example, if a drug researcher runs multiple studies to study if a drug is harmful to a patient, they would summarize findings associated with each study to show that on average the drug has very few harmful effects. Comparative analysis compares or contrasts the findings of similar studies. However, in both of the above approaches, the studies must all be directly related or similar to each other.

Accordingly, there remains a need for a system and a method to combine and analyze research studies that have different collection methods, different respondents, ask different questions or different variable types, and have findings that are different from each other.

SUMMARY

This summary is provided to introduce a selection of concepts in a simplified form that are further disclosed in the detailed description. This summary is not intended to determine the scope of the claimed subject matter.

The embodiments herein address the above-recited needs system and a method to combine and analyze research studies that have different collection methods, different respondents, ask different questions or different variable types, and have findings that are different from each other.

In one aspect, a processor-implemented method for joining two or more research studies to extract analytical insights for enabling cross-study analysis is disclosed. The method includes identifying, using an identification module, at least one matched variable in a statistically representative sample in each of the two or more research studies. The method further includes establishing, using a segment establishing module, for each combination of matched variables, a schema of segments, from the two or more research studies. As used herein the term "schema" represents a unique combination of matched variables from one or more research studies. Each schema results in creation of two or more segments, where each combination of individual values of variables creates each segment. As used herein the term "statistically representative" segments refers to a representative sample which is a subset of a population that seeks to accurately reflect predetermined characteristics of a larger group. The method further includes determining, using the segment establishing module if each of the established schema of segments is statistically representative. The method further includes creating a joint study, using a joint study creation module, by combining responses from each of the two or more research studies within each segment of the statistically representative schema of segments. The joint study may be used by a user for performing a cross-study analysis by extracting analytical insights from the joint study.

In an embodiment, a step of creating the joint study includes determining a combination of matched variable segments associated with the highest number of variables, that have statistically representative samples based on a predetermined confidence level and evaluating each variable combination that is also statistically representative of the population for combining responses from each of the two or more research studies within each segment of the statistically representative schema of segments.

In an embodiment, a step of creating the joint study includes determining a combination of matched variable segments associated with the highest number of variables, that have statistically representative samples based on a predetermined confidence level, receiving a user selected variable to import and determine one or more variables that are related with each other and establish terms of relationship between the one or more variables, and changing outliers and unexpected values to be within a predetermined range and delete erroneous data, for combining responses from each of the two or more research studies within each segment of the statistically representative schema of segments.

In an embodiment, establishing the schema of segments includes creating a list of schemas from each of the two or more research studies, running through each schema from the list of schemas, and defining one or more segments in data sets corresponding to the two or more research studies, determining if each segment passes predetermined statistical testing; and recommending schema based on the result of the predetermined statistical testing for each of the data sets.

In an embodiment, recommending the schema includes selecting a schema that satisfies at least one of the following criteria: a) passes a sample size test for each of the data sets, b) comprises the longest combination of matched variables in the schema, and c) comprises the highest percentage of segments that passed a p-value test. Upon two schemas having the same percentage of segments, an average p-value test is taken and the segment with the highest average p-value is selected.

In an embodiment, the one or more matched variable segments have one or more common traits and behavioral attributes.

In an embodiment, identifying one or more matched variables includes classifying a plurality of variables by name, implementing a meta-tagging from a wish list, matching variables that are similar, providing one or more suggestions of matched variables for selection by a user based on one or more pre-populated lists, receiving a confirmation of the selection by the user, determining if values between the variables can be matched among the matched variables, determining variables that are similar using fuzzy matching, and receiving matching of one or more remaining values from the user.

In an embodiment, determining if the established schema of segments is statistically representative includes identifying one or more schema as a combination of matched variables, based on the number of responses for each possible segment, determining if the resulting segments in each schema are statistically representative, and identifying the deepest combination of matched variables that have significant samples.

In an embodiment, identifying the deepest combination of matched segments includes a) determining a minimum sample size per segment that is constant over all the segments, b) verifying if there is a correlation between structures of two datasets by the segments, and c) combining the results of the steps a) and b) to determine the best segmentation.

In an embodiment, determining the minimum sample size includes running an algorithm with a margin of error and the confidence level that defines the value of confidence level as a variable, generating a list of matching variable combinations that assures that the minimum sample size requirement is met for one or more segments and matching scheme with the best margin of error and confidence level chosen as optimal.

In an embodiment, a step of verifying if there is a correlation includes a) defining a correlation metric that can show how close two distributions are to one another, b) choosing a matching scheme with the highest correlation coefficient or the lowest p-value for the chi-square as a winning scheme, and c) combining the results of the steps a) and b).

In another aspect, a system for joining two or more research studies to extract analytical insights for enabling cross-study analysis is disclosed. The system includes a memory and a processor. The memory stores non-transitory executable instructions and one or more executable modules. The processor executes one or more executable modules for joining two or more research studies to extract analytical insights for enabling cross-study analysis. One or more executable modules include an identification module, a segment establishing module, and a joint study creation module. The identification module is configured to identify at least one matched variable in a statistically representative sample in each of the two or more research studies. The segment establishing module is configured to establish for each combination of matched variables, a schema of segments, from the two or more research studies and determine if each of the established schema of segments is statistically representative. The joint study creation module is configured for creating a joint study by combining responses from each of the two or more research studies within each segment of the statistically representative schema of segments.

In an embodiment, the segment establishing module is further configured for: creating a list of schemas from each of the two or more research studies, running through each schema and defining all segments in data sets corresponding to the two or more research studies, determining if each segment passes a predetermined statistical testing, and recommending schema based on the result of the predetermined statistical testing for each of the data sets.

In an embodiment, the segment establishing module is further configured for: selecting schema that at least one of: a) passes a sample size test for each of the data sets, b) comprises the longest combination of matched variables in the schema, and c) comprises the highest percentage of segments that passed a p-value test. Upon two schemas having the same percentage of segments, an average p-value test is taken and the segment with the highest average p-value is selected.

In an embodiment, the one or more matched variable segments have one or more common traits and behavioral attributes.

In an embodiment, the identification module is further configured for:
  classifying a plurality of variables by name;
  implementing a meta-tagging from a wish list;
  matching variables that are similar;
  providing one or more suggestions of matched variables for selection by a user based on one or more pre-populated lists;
  receiving a confirmation of the selection by the user;
  determining if values between the variables can be matched among the matched variables;
  determining variables that are similar using fuzzy matching; and
  receiving matching of one or more remaining values from the user.

In an embodiment, the segment establishing module is further configured for identifying one or more schema as a combination of matched variables, based on the number of responses for each possible segment, determining if the resulting segments in each schema are statistically representative, and identifying the deepest combination of matched variables that have significant samples.

In an embodiment, identifying the deepest combination of matched segments includes: a) determining a minimum sample size per segment that is constant over all the segments, b) verifying if there is a correlation between structures of two datasets by the segments, and c) combining the results of the steps a) and b) to determine the best segmentation.

In an embodiment, determining the minimum sample size includes running an algorithm with a margin of error and the confidence level that defines the value of confidence level as a variable, generating a list of matching variable combinations that assures that the minimum sample size requirement is met for one or more segments, and matching scheme with the best margin of error and confidence level chosen as optimal.

In an embodiment, verifying if there is a correlation includes a) defining a correlation metric that can show how close two distributions are to one another, b) choosing a matching scheme with the highest correlation coefficient or the highest p-value for the chi-square as a winning scheme, and c) combining the results of the steps a) and b).

In yet another aspect, one or more non-transitory computer-readable storage mediums storing one or more sequences of instructions, which when executed by one or more processors, causes a method of joining two or more research studies to extract analytical insights for enabling cross-study analysis. The method includes identifying, using an identification module, at least one matched variable in a statistically representative sample in each of the two or more research studies. The method further includes establishing, using a segment establishing module, for each combination of matched variables, a schema of segments, from the two or more research studies. The method further includes determining, using the segment establishing module if each of the established schema of segments is statistically representative. The method further includes creating a joint study, using a joint study creation module, by combining responses from each of the two or more research studies within each segment of the statistically representative schema of segments.

Various embodiments of the present technology enable combining and analyzing two or more research studies that have different collection methods, different respondents, ask different questions or different variable types, and have findings that are different from each other. The present technology eliminates potential erroneous data and develops estimates for what respondents intend to answer and requires user guidance. The present technology preserves complete response data and can be automated and run continuously.

In one or more embodiments, related systems comprise circuitry and/or programming for executing the methods disclosed herein. The circuitry and/or programming are of any combination of hardware, software, and/or firmware configured to execute the methods disclosed herein depending upon the design choices of a system designer. In an embodiment, various structural elements are employed depending on the design choices of the system designer.

BRIEF DESCRIPTION OF THE DRAWINGS

The embodiments herein will be better understood from the following detailed description with reference to the drawings, in which:

The foregoing summary, as well as the following detailed description, is better understood when read in conjunction with the appended drawings. For illustrating the embodiments herein, exemplary constructions of the embodiments are shown in the drawings. However, the embodiments herein are not limited to the specific components and methods disclosed herein. The description of a component or a method step referenced by a numeral in a drawing is applicable to the description of that component or method step shown by that same numeral in any subsequent drawing herein.

Figure 1:
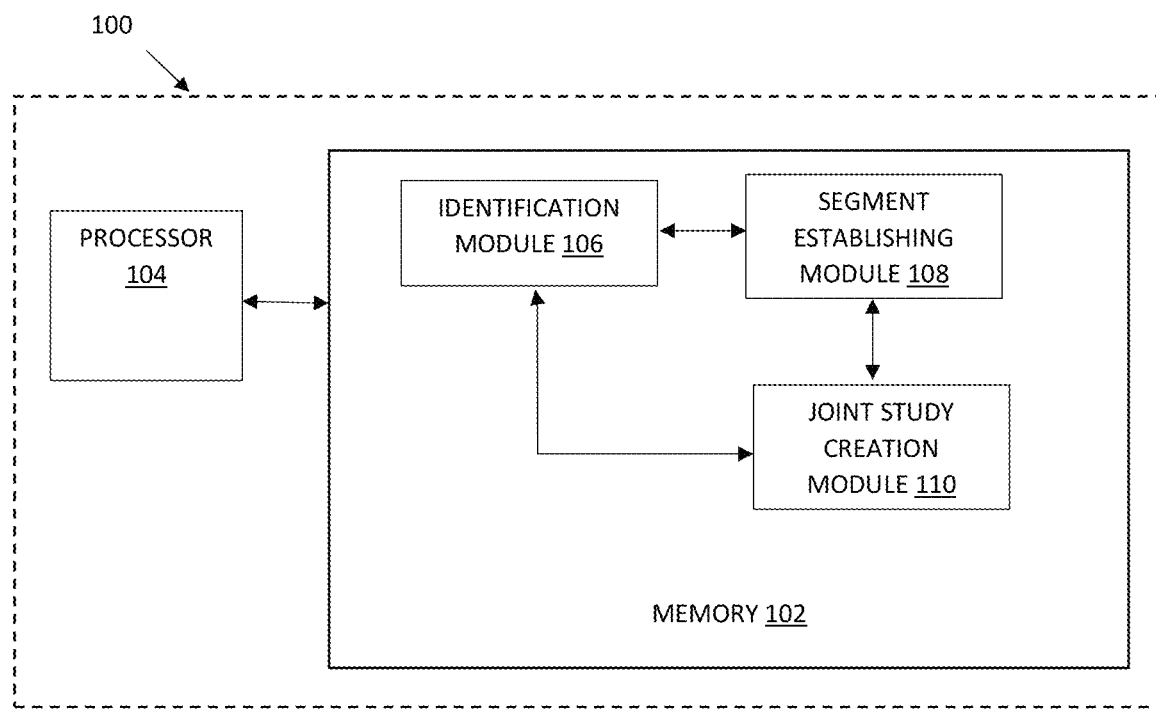
Figure 2B:
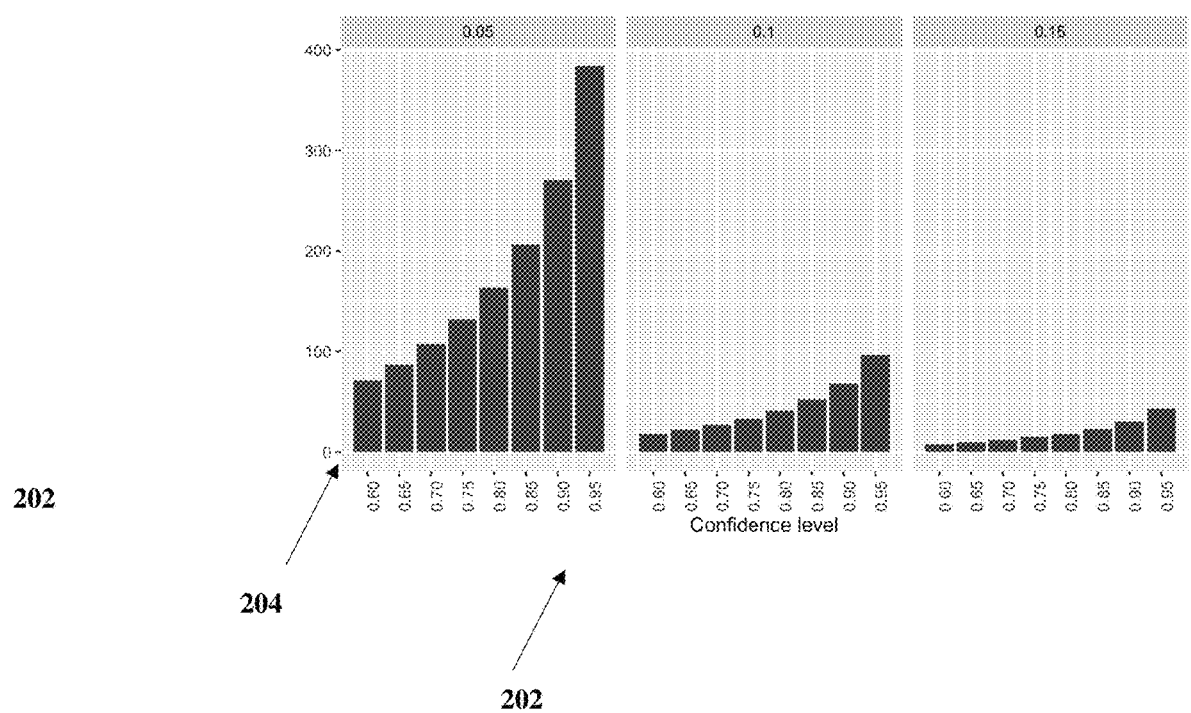
Figure 3A:
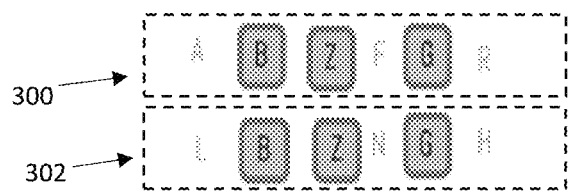
Figure 3B:
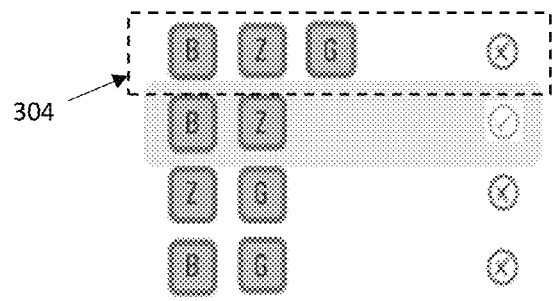
Figure 3C:
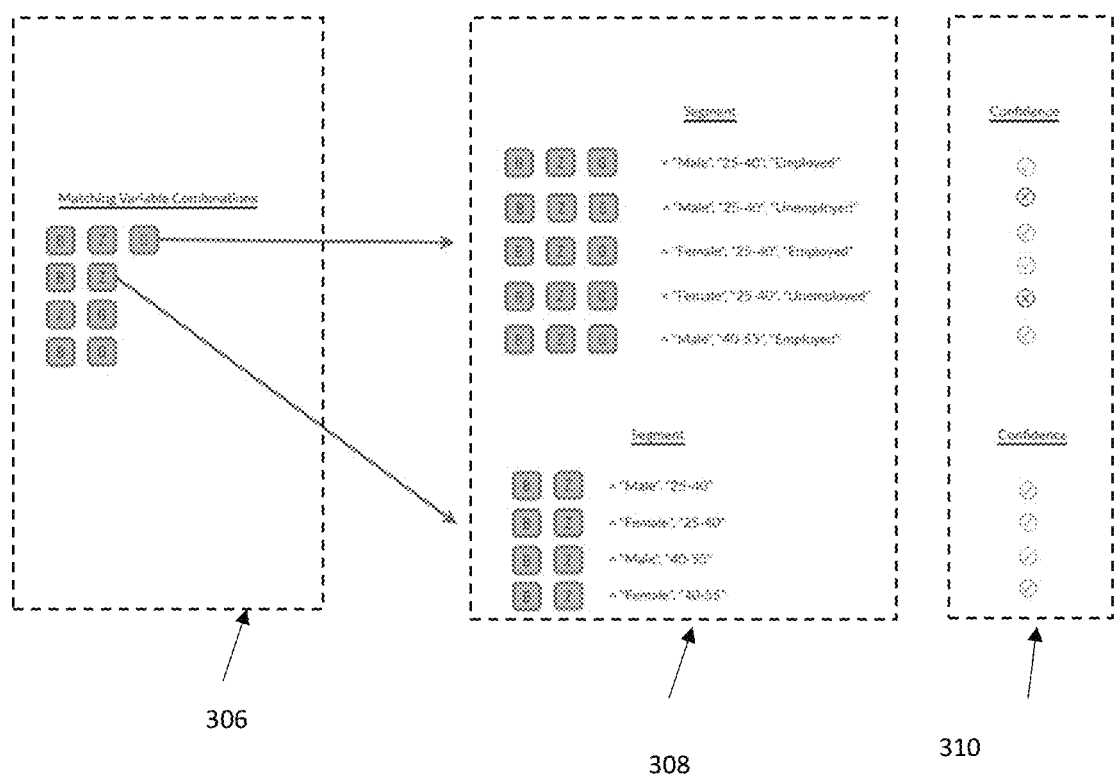
Figure 3D:
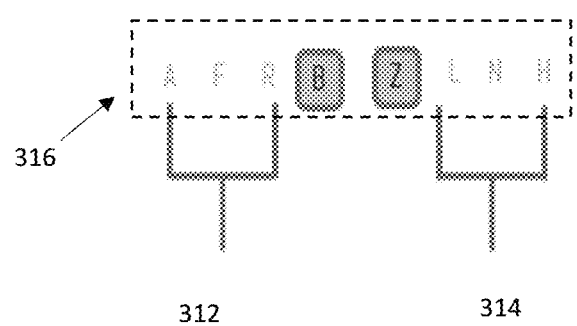
Figure 4A:
Figure 5:
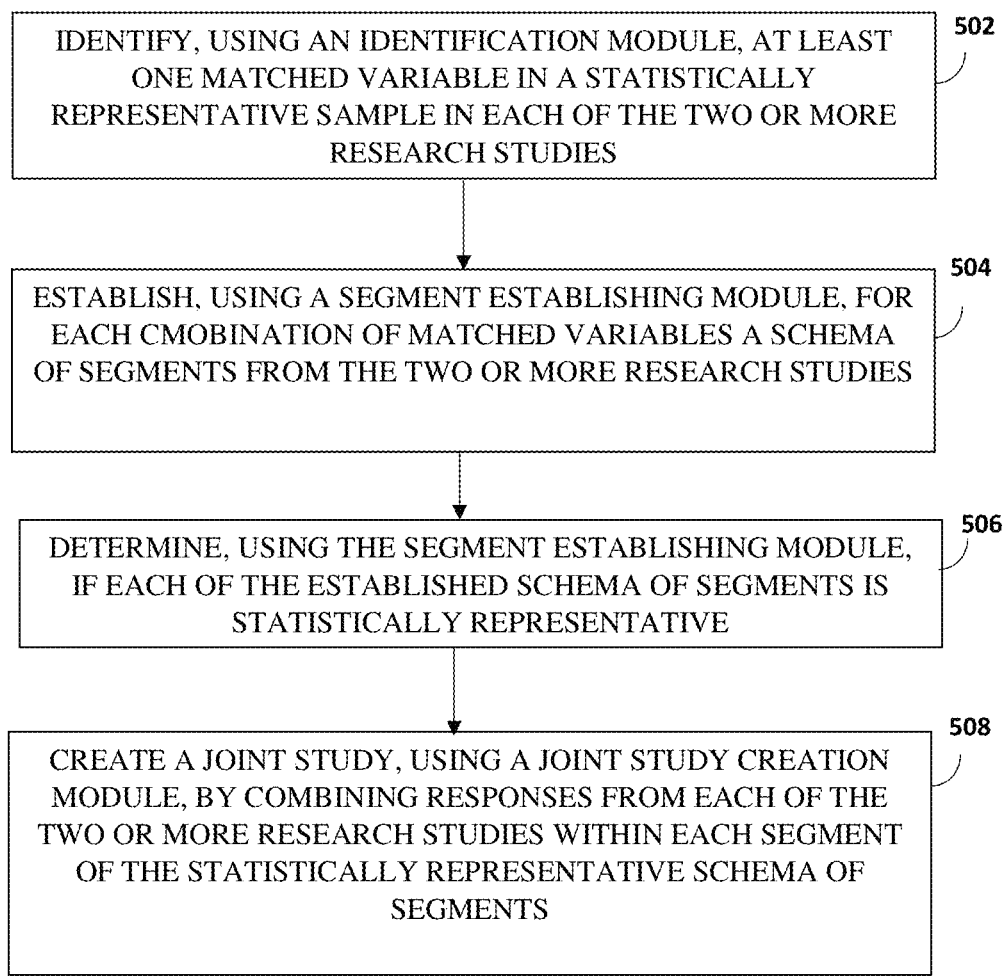

The embodiments herein will be better understood from the following detailed description with reference to the drawings, in which:

FIG. 1 depicts a system for joining two or more research studies to extract analytical insights for enabling cross-study analysis, in accordance with an embodiment;

FIG. 2A depicts a frequency distribution by segments among two datasets, in accordance with an exemplary scenario;

FIG. 2B depicts exemplary graphs of confidence levels plotted along the x-axis against a sample size plotted along the y-axis, in accordance with an exemplary scenario;

FIG. 2C depicts a table illustrating a change in sample size with varying values of Z for a given margin of error, in accordance with an exemplary scenario;

FIG. 2D depicts a table illustrating two example datasets, in accordance with an exemplary scenario;

FIG. 2E illustrates a table showing gender listed against education, in accordance with an exemplary scenario;

FIG. 2F illustrates the results of a Chi-square test, in accordance with an exemplary scenario;

FIG. 2G illustrates a table showing the results of a hypothesis test, in accordance with an exemplary scenario;

FIGS. 3A-3C illustrate an exemplary scenario of two research studies to extract analytical insights for enabling cross-study analysis, in accordance with an exemplary scenario;

FIG. 3D illustrates creating a joined study, in accordance with an exemplary scenario;

FIG. 4A-4B depict exemplary tables created for a schema of segments, in accordance with an exemplary scenario; and FIG. 5 depicts a flow diagram that illustrates a method of joining two or more research studies to extract analytical insights for enabling cross-study analysis, in accordance with an embodiment.

DETAILED DESCRIPTION OF PREFERRED EMBODIMENTS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Various embodiments of the present technology enable combining and analyzing two or more research studies that have different collection methods, different respondents, ask different questions or different variable types, and have findings that are different from each other. The present technology eliminates potential erroneous data and develops estimates for what respondents intend to answer and requires user guidance. The present technology preserves complete response data and can be automated and run continuously. The joint study allows a user to extract analytical insights for enabling cross-study analysis FIG. 1 depicts a system for joining two or more research studies to extract analytical insights for enabling cross-study analysis, in accordance with an embodiment. The system 100 includes a memory 102 and a processor 104. The memory 102 stores non-transitory executable instructions and one or more executable modules. The processor 104 executes one or more executable modules for joining two or more research studies to extract analytical insights for enabling cross-study analysis. The one or more executable modules include an identification module 106, a segment establishing module 108, a joint study creation module 110, and a cross-study analysis module 112. The identification module 106 is configured for identifying at least one matched variable in a statistically representative sample in each of the two or more research studies. The segment establishing module 108 is configured for establishing for each combination of matched variables, a schema of segments, from the two or more research studies and determining if each of the established schema of segments is statistically representative. As used herein the term "schema" represents a unique combination of matched variables from one or more research studies. Each schema (shown as 306, in FIG. 3C, such as for example schema B Z G, schema B Z, schema Z G, and schema B G) results in creation of two or more segments (shown as 308, in FIG. 3C), where each combination of individual values of variables creates each segment. As used herein the term "statistically representative" segments refers to a representative sample which is a subset of a population that seeks to accurately reflect predetermined characteristics of a larger group. For example, if in a given population, 60% are in the income bracket of [50K, 100K] and we have the same proportion in the sample segment, it means that the sample segment is statistically representative of the given population. The one or more matched variable segments have one or more common traits and behavioral attributes.

In an embodiment, the segment establishing module 108 is further configured for creating a list of schemas from each of the two or more research studies, running through each schema and defining all segments in data sets corresponding to the two or more research studies, determining if each segment passes a predetermined statistical testing, and recommending schema based on the result of the predetermined statistical testing for each of the data sets. The segment establishing module 108 is further configured for selecting a schema that at least satisfies one of the following criteria: a) passes a sample size test for each of the data sets, b) comprises the longest combination of matched vars in the schema, and c) comprises the highest percentage of segments that passed a p-value test. In an embodiment, upon two schemas having the same percentage of segments, an average p-value test is taken and the segment with the highest average p-value is selected.

The joint study creation module 110 is configured for creating a joint study, by combining responses from each of the two or more research studies within each segment of the statistically representative schema of segments. The system 100 enables a user to perform a cross-study analysis by extracting analytical insights from the joint study.

The joint study creation module 110 is configured to create the joint study by determining a combination of matched variable segments associated with the highest number of variables, that have statistically representative samples based on a predetermined confidence level and evaluating each variable combination that is also statistically representative of the population for combining responses from each of the two or more research studies within each segment of the statistically representative schema of segments.

The joint study creation module 110 is configured to create the joint study by determining a combination of matched variable segments associated with the highest number of variables, that have statistically representative samples based on a predetermined confidence level, receiving a user-selected variable to import and determine one or more variables that are related with each other and establish terms of relationship between the one or more variables, and changing outliers and unexpected values to be within a predetermined range and delete erroneous data, for combining responses from each of the two or more research studies within each segment of the statistically representative schema of segments.

The identification module 106 is further configured for classifying a plurality of variables by name, implementing a meta-tagging from a wish list, matching variables that are similar, providing one or more suggestions of matched variables for selection by a user based on one or more pre-populated lists, receiving a confirmation of the selection by the user, determining if values between the variables can be matched among the matched variables, determining variables that are similar using fuzzy matching, and receiving matching of one or more remaining values from the user.

The segment establishing module 108 is further configured for identifying one or more schema as a combination of matched variables, based on the number of responses for each possible segment. The segment establishing module 108 determines if the resulting segments in each schema are statistically representative. The segment establishing module 108 identifies the deepest combination of matched variables that have significant samples. Identifying the deepest combination of matched segments includes a) determining a minimum sample size per segment that is constant over all the segments, b) verifying if there is a correlation between structures of two datasets by the segments, and c) combining the results of the steps a) and b) to determine a best segmentation. In an embodiment, verifying if there is a correlation includes a) defining a correlation metric that can show how close two distributions are to one another, b) choosing a matching scheme with the highest correlation coefficient or the highest p-value for the chi-square as a winning scheme, and c) combining the results of the steps a) and b).

In an embodiment, determining the minimum sample size includes running an algorithm with a margin of error and the confidence level that defines the value of confidence level as a variable, generating a list of matching variable combinations that assures that the minimum sample size requirement is met for one or more segments, and matching scheme with the best margin of error and confidence level chosen as optimal.

The minimum sample size is computed using one or more techniques.

$$n = \frac{Z_{\alpha/2}^2 * \sigma^2}{e^2} \quad (1)$$

In an embodiment, equation (1) is used when the population mean needs to be estimated. However, as the sigma square (population variance) is usually unknown, in another embodiment, minimum sample size formula for proportions based on equation (2) is used.

In an embodiment, the minimum sample size is determined based on the equation (2):

$$n = \frac{Z_{\alpha/2}^2 \pi(1-\pi)}{e^2} \quad (2)$$

wherein Z is a confidence level and sigma is the population variance, e is the margin of error, the value of pi is taken as 0.5.

In an embodiment, verifying if there is a correlation includes a) defining a correlation metric that can show how close two distributions are to one another, b) choosing a matching scheme with the highest correlation coefficient or the highest p-value for the chi-square as a winning scheme, and c) combining the results of the steps a) and b).

For example, consider the frequency distribution by segments among two datasets as depicted in FIG. 2A. A correlation metric is defined based on a simple person correlation coefficient or based on a Chi-square test. The Chi-square test generates two variables that are independent and thus proportions do not significantly differ from each other. The results of the simple person correlation coefficient and the Chi-square test are combined to obtain the correlation metric.

FIG. 2B depicts graphs of confidence level 202 plotted along the x-axis against a sample size 204 plotted along the y-axis, for margin of errors of 5%, 10%, and 15%, in accordance with an exemplary scenario. The graphs depict the change in sample size with varying values of Z for a given margin of error. Consider for example if the margin of error is 5%, the change in sample size with the value of change in Z (the confidence level) is as shown in FIG. 2A. The significance level and the margin of error can be chosen. In another embodiment, a representative sample of the population is used to compute the minimum sample size, when the population proportions are known. In an embodiment, the population proportions are specified by the user.

For example, in the table depicted in FIG. 2C, there are two variables listed in Columns A and B, Column C lists the corresponding proportions in the sample and Column D shows the proportions in the population. Column D is specified by a user. Usually, the user will not have proportions by groups, but will have only marginal proportions (% males, % females, % Basic, % Advanced, and the like), the system 100 estimates joint proportions based on marginal props. Subsequently, the system 100 determines whether the sample and population proportions are correlated.

In another embodiment, the system 100 correlates the data sets in one or more research studies based on the frequency distributions in each of the data sets.

FIG. 2D depicts a table illustrating two example datasets, in accordance with an exemplary scenario. For example, consider when two variables are used in the joining process, in the following table.

FIG. 2E illustrates a table showing gender (F/M), and age (e.g., 20-25) listed against education, in accordance with an exemplary scenario. In an embodiment, the system 100 looks at the correlations between frequencies or performs a Chi-square. FIG. 2F illustrates the results of a Chi-square test, in accordance with an exemplary scenario.

FIG. 2G illustrates a table showing the results of a hypothesis test, in accordance with an exemplary scenario. In yet another embodiment, the system 100 uses a third numeric variable as a test variable. Consider, for example, the third variable is income. The system 100 performs a hypothesis test for each segment between the dataset on the equality of means, then determines how many times the hypothesis is rejected, where non-rejection shows that segmentation is good.

The system 100 matches respondents in both the research studies using the segments, as shown in the table of FIG. 2G. The system 100 creates joined studies with respondents in the same segment by appending values using a complete (unaltered) data set.

In an embodiment, the segment establishing module 108 creates a list of potential schemas (segment variables) in each of the research studies, runs through each schema, defines all segments in data sets, and then determines if each segment passes the statistical testing. The statistical testing may include, for example, sample size test and proportion test. The statistical test includes using a confidence level of a predetermined value, such as for example 0.8, and selecting a predetermined margin of error of for example 0.1. In an embodiment, at least 0.90 of segments must pass the above test for the segment schema to be used, in both data sets. The system 100 alerts the user if an attempt is made by the user to analyze data from a segment that does not pass the sample size test.

The system 100 tests different schemas and returns the number of segments that pass the sample size test and the share of these segments in the total number of segments per database. For example, for the schema ['gender', 'age', 'educ'] in the first sample 22 segments (92% of the segments) pass the sample size test, and for the second segment, 14 (58% of the segments) pass the sample size test.

```
: [ [ [ ['gender', 'age'], 6, 1.0],
    [ ['gender', 'educ'], 8, 1.0],
    [ ['age', 'educ'] 12, 1.0],
    [ ['gender', 'age', 'educ'], 22, 0.92] ],
  [ [ ['gender', 'age'], 6, 1.0],
    [ ['gender', 'educ'], 8, 1.0],
    [ ['age', 'educ'], 12, 1.0],
    [ ['gender', 'age', 'educ'], 14, 0.58 ] ] ]
```

In an embodiment, the proportions test includes grabbing the proportion for each segment that is created from the schema. The segment establishing module 108 runs sig testing on all proportions (z test for proportions) and determines if the proportions are roughly equivalent. The result of the proportions test is a p-value. The p-value should be greater than 0.1. If any segment fails the test, the system 100 notifies the user of which segments did not PASS and the amount. The amount is quantified as the percentage of segments that passed the p-value test. In an embodiment, a sample size for the proportions test is given by equation (2):

$$n = \frac{Z_{\alpha/2}^2 \pi(1-\pi)}{e^2} \quad (2)$$

The system 100 tests if this results in equal to or less than the number of respondents in each segment. The system 100 plays with the confidence and margin to break the tie of the schemas. Consider, for example, matching two datasets: ANES (American National Election studies—2022) and the environment disposition survey (EDS 2019). The matching variables are: gender, education, and marital status.
The results of the schema search are given below:
Samples Test:

```
[ [ [ ['gender', 'educ'], 8, 0.8],
    [ ['gender', 'marital'], 6, 0.6],
    [ ['educ', 'marital'], 11, 0.46],
    [ ['gender', 'educ', 'marital'], 15, 0.32] ],
  [ [ ['gender', 'educ'], 10, 1.0],
    [ ['gender', 'marital'], 9, 0.9],
    [ ['educ', 'marital'], 17, 0.68],
    [ ['gender', 'educ', 'marital'], 26, 0.52] ] ]
```

The results of the proportion test (for alpha=0.05) are given below:

```
: [ [ ('gender', 'educ'), 2, 10, 0.2, 0.25713559421301635],
    [ ('gender', 'marital'), 3, 10, 0.3, 0.34811225103118704],
    [ ('educ', 'marital') , 4, 25, 0.16, 0.3779993107359238],
    [ ('gender', 'educ', 'marital'), 5, 50, 0.1, 0.4339786044083694] ]
```

It can be observed from the above example, that for the [gender, educ] variable combination there are two segments for which the proportion test is rejected, overall, there are 10 segments, and rejected segments comprise 20% of all the segments, with an average p-value of 0.25.

In an embodiment recommending the schema includes selecting a schema that is at least one of:
a) passes a sample size test for each of the data sets;
b) comprises the longest combination of matched vars in the schema; and c) that comprises the highest percentage of segments that passed a p-value test.

Upon two schemas having the same percentage of segments, an average p-value test is taken and the segment with the highest average p-value is selected.

FIG. 3A illustrates matching similar variables in two research studies, in accordance with an exemplary scenario. More particularly, FIG. 3B depicts the variables A, B, Z, F, G, and R of a first research study "Survey A" 300, and the variables L, B, Z, G, and H of a second research study "Survey B" 302. The system establishes segments in each of the first research study 300 and the second research study by establishing matching variables, such as B, Z, and G, that are found in both the research studies, so that they are the same. The system identifies segments as a combination of matched variables and looks at the number of responses for each possible segment. FIG. 3B illustrates the identification of segments as a combination of matched variables, in accordance with an exemplary scenario. The system uses a confidence level (for example, 0,90) to determine if each segment is statistically representative. For instance, as depicted in FIG. 3B, the combination 304 of the variables B and Z, has a better confidence level compared to other combinations. The system determines the deepest combination of matched variable segments that have significant samples based on the confidence level. FIG. 3C depicts evaluating matching variable combinations, in accordance with an exemplary scenario. Also, FIG. 3C depicts a schema of segments 306 and segments 307 comprising a list of variables such that a combination of individual values of variables creates each segment. As depicted in FIG. 3C, each variable combination is evaluated to find the most detailed combination that is also statistically representative of the population. For the matching variable combinations 306 B, Z, G and B, Z, some example segments 308 such as, "Male", "25-40", "employed" or "Male", "25-40", and the like may be obtained. The corresponding confidence levels 310 for the segments are also depicted in FIG. 3C. The tick mark indicates that the segments are representative, and the cross mark indicates that the segments are not representative.

The system 100 creates joined study based on representative segments. The system 100 combines/merges results by matching responses in both the research studies, using respondents in the same representative segment. FIG. 3D illustrates creating a joined study, in accordance with an exemplary scenario. The system 100 appends values using a complete (unaltered) data set-assuming that the two responses were from the same respondent and data set. For example, the system 100 joins the matched variable segments from survey A 312 and survey B 314 to create a joined study 316 (survey AB).

In another embodiment, the system 100 eliminates outliers in individual response data and margins the research studies using normalized expected values. In an embodiment, the system 100 establishes matched variables that are found in both the research studies. The system 100 standardizes values in two or more research studies so that they are the same. The system 100 identifies segments as a combination of matched variables and checks the number of responses for each possible segment. The system 100 uses a confidence level (0,90) to determine if each segment is statistically representative. The system 100 finds the deepest combination of matched variable segments that have significant samples and uses the combination of the matched variables for matching respondents in two or more research studies. The system 100 establishes the expected values. In an embodiment, a user selects the most important variables to import and the system 100 determines which of the selected important variables are related to each other and establishes terms of the relationship. The system 100 changes all outlier and unexpected values to be within the acceptable and expected range. The system 100 deletes clearly the erroneous data when appropriate. The system 100 creates joined study by combining the results by matching responses in both the studies and joining the two or more research studies by using respondents in the same segment. The system 100 appends the values using normalized values from the data set. The system 100 eliminates potential erroneous data and develops estimates for what respondents intend to answer and requires user guidance.

FIG. 4A depicts an exemplary table created for a schema of segments, in accordance with an exemplary scenario. The table 400 includes column 402 corresponding to "gender" and "age", column 404 corresponding to "gender" and "education", column 406 corresponding to "age" and "education", and column 408 corresponding to "gender" "age" and "education". The table also shows a corresponding number of segments created, a sample size of segments that passed the sample size test, a percentage of segments that passed the proportions test with an average p-value, and an average p-value for the means test per variable.

FIG. 4B depicts an exemplary table 410 including column 412 corresponding to "gender" and "age", column 414 corresponding to "gender" and "education", column 416 corresponding to "age" and "education", and column 418 corresponding to "gender" "age" and "education. In this example, the system 100 takes on the study and divided up the number of variables in half, and then selects 4-5 variables that will be shared in each study (that include the matched variables). The system 100 randomly removes 25% of responses and runs an algorithm to create joint studies.

After joining datasets, the system 100 apples a t-test on the quality of the means for the segments. Consider, for example, a numeric variable K, as the system 100 creates a new dataset by randomly selecting 75% of the cases, and then joining a new dataset with the first one, one would assume that the means of K in these two datasets by segments should not differ from each other significantly. The result for the schema [gender, age, educ] is given below.

Schema: ['gender', 'age', 'educ']
Samples test for two dataframes [ [ ['gender', 'age', 'educ'], 22, 0.92], [ ['gender', 'age', 'educ'], 15, 0.62] ]
Proportions test [ ('gender', 'age', 'educ'), 0, 24, 0.0, 0.7797484913102118]

| means gender1 | age1 | educ1 | K1 | K2 |
|---|---|---|---|---|
| F | [20-25] | Advanced | 10.454146 | 9.578293 |
|   |         | Basic | 10.228000 | 11.094000 |
|   |         | Intermediate | 11.062273 | 11.984091 |
|   |         | Less than B | 9.579592 | 10.354286 |
|   | [26-30] | Advanced | 8.866806 | 8.341389 |
|   |         | Basic | 10.007692 | 10.223385 |
|   |         | Intermediate | 9.796222 | 9.602000 |
|   |         | Less than B | 9.853400 | 10.412200 |
|   | [31-35] | Advanced | 9.600149 | 10.088060 |
|   |         | Basic | 10.383956 | 10.512747 |
|   |         | Intermediate | 10.038205 | 10.486154 |
|   |         | Less than B | 11.146557 | 10.940492 |
| M | [20-25] | Advanced | 9.245333 | 9.196000 |
|   |         | Basic | 10.359701 | 11.309403 |
|   |         | Intermediate | 10.969310 | 10.949655 |
|   |         | Less than B | 9.513167 | 10.454333 |
|   | [26-30] | Advanced | 10.411231 | 11.082154 |
|   |         | Basic | 9.965600 | 10.196900 |

-continued

Schema: ['gender', 'age', 'educ']
Samples test for two dataframes [ [ ['gender', 'age', 'educ'],
22, 0.92], [ ['gender', 'age', 'educ'], 15, 0.62] ]
Proportions test [ ('gender', 'age', 'educ'),
0, 24, 0.0, 0.7797484913102118]

means

| gender1 | age1 | educ1 | K1 | K2 |
|---|---|---|---|---|
| | [31-35] | Intermediate | 10.871190 | 9.892381 |
| | | Less than B | 10.565926 | 10.866543 |
| | | Advanced | 10.082796 | 10.425161 |
| | | Basic | 10.341810 | 9.728534 |
| | | Intermediate | 9.480000 | 9.467333 |
| | | Less than B | 11.386220 | 11.269024 | number of segments 24
Results of mean comparison, p-value 0.6284874790262112

As demonstrated, the average p-value across all pairwise comparisons for the means test is 0.62, which confirms that the two datasets are coming from the same population.

FIG. 5 depicts a flow diagram that illustrates a method of joining two or more research studies to extract analytical insights for enabling cross-study analysis, in accordance with an embodiment. In an embodiment at step 502, using an identification module 106, at least one matched variable is identified in a statistically representative sample in each of the two or more research studies. In step 504, for each combination of matched variables, a schema of segments is established, from the two or more research studies, using a segment establishing module 108. At step 506, using the segment establishing module, it is determined if each of the established schema of segments is statistically representative. At step 508, a joint study is created using a joint study creation module 110, by combining responses from each of the two or more research studies within each segment of the statistically representative schema of segment.

In an embodiment, a step of creating the joint study includes determining a combination of matched variable segments associated with the highest number of variables, that have statistically representative samples based on a predetermined confidence level and evaluating each variable combination that is also statistically representative of the population for combining responses from each of the two or more research studies within each segment of the statistically representative schema of segments.

In an embodiment, a step of creating the joint study includes determining a combination of matched variable segments associated with the highest number of variables, that have statistically representative samples based on a predetermined confidence level (for example, 0.8), receiving a user-selected variable to import and determine one or more variables that are related with each other and establish terms of relationship between the one or more variables, and changing outliers and unexpected values to be within a predetermined range and delete erroneous data, for combining responses from each of the two or more research studies within each segment of the statistically representative schema of segments.

In an embodiment, establishing the schema of segments includes creating a list of schemas from each of the two or more research studies, running through each schema from the list of schemas, and defining one or more segments in data sets corresponding to the two or more research studies, determining if each segment passes a predetermined statistical testing; and recommending schema based on the result of the predetermined statistical testing for each of the data sets.

In an embodiment, recommending the schema includes selecting a schema that at least satisfies one of the following criteria: a) passes a sample size test for each of the data sets, b) comprises the longest combination of matched vars in the schema, and c) comprises the highest percentage of segments that passed a p-value test. Upon two schemas having the same percentage of segments, an average p-value test is taken and the segment with the highest average p-value is selected.

In an embodiment, the one or more matched variable segments have one or more common traits and behavioral attributes. In an embodiment, identifying one or more matched variables includes classifying a plurality of variables by name, implementing a meta-tagging from a wish list, matching variables that are similar, providing one or more suggestions of matched variables for selection by a user based on one or more pre-populated lists, receiving a confirmation of the selection by the user, determining if values between the variables can be matched among the matched variables, determining variables that are similar using fuzzy matching, and receiving matching of one or more remaining values from the user.

In an embodiment, determining if the established schema of segments is statistically representative includes identifying one or more schema as a combination of matched variables, based on the number of responses for each possible segment, determining if the resulting segments in each schema are statistically representative, and identifying the deepest combination of matched variables that have significant samples.

In an embodiment, identifying the deepest combination of matched segments includes: a) determining a minimum sample size per segment that is constant over all the segments, b) verifying if there is a correlation between structures of two datasets by the segments, and c) combining the results of the steps a) and b) to determine the best segmentation.

In an embodiment, determining the minimum sample size includes running an algorithm with a margin of error and the confidence level that defines the value of confidence level as a variable, generating a list of matching variable combinations that assures that the minimum sample size requirement is met for one or more segments, and matching scheme with the best margin of error and confidence level chosen as optimal.

In an embodiment, verifying if there is a correlation includes: a) defining a correlation metric that can show how close two distributions are to one another, b) choosing a matching scheme with the highest correlation coefficient or the highest p-value for the chi-square as a winning scheme, and c) combining the results of the steps a) and b).

Various embodiments of the present technology enable combining and analyzing two or more research studies that have different collection methods, different respondents, ask different questions or different variable types, and have findings that are different from each other. The present technology eliminates potential erroneous data and develops estimates for what respondents intend to answer and requires user guidance. The present technology preserves complete response data and can be automated and run continuously. The joint study allows a user to extract analytical insights for enabling cross-study analysis.

As will be readily apparent to those skilled in the art, the present invention may easily be produced in other specific forms without departing from its essential characteristics. The present embodiments are, therefore, to be considered as merely illustrative and not restrictive, the scope of the invention being indicated by the claims rather than the foregoing description, and all changes which come within therefore intended to be embraced therein.

A "non-transitory computer-readable medium" for purposes of embodiments of the present invention may be any medium that can contain, store, communicate, propagate, or transport the program for use by or in connection with the instruction execution system, apparatus, system, or device. The computer-readable medium can be, by way of example only but not by limitation, an electronic, magnetic, optical, electromagnetic, infrared, or semiconductor system, apparatus, system, device, propagation medium, or computer memory.

A "processor" or "process" includes any human, hardware and/or software system, mechanism or component that processes data, signals, or other information. A processor can include a system with a general-purpose central processing unit, multiple processing units, dedicated circuitry for achieving functionality, or other systems. Processing need not be limited to a geographic location or have temporal limitations. For example, a processor can perform its functions in "real-time," "offline," in a "batch mode," etc. Portions of processing can be performed at different times and at different locations, by different (or the same) processing systems.

The embodiments herein can take the form of, an entirely hardware embodiment, an entirely software embodiment, or an embodiment including both hardware and software elements. The embodiments that are implemented in software include but are not limited to, firmware, resident software, microcode, and the like. Furthermore, the embodiments herein can take the form of a computer program product accessible from a computer-usable or computer-readable medium providing program code for use by or in connection with a computer or any instruction execution system. For the purposes of this description, a computer-usable or computer-readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid-state memory, magnetic tape, a removable computer diskette, a random-access memory (RAM), a read-only memory (ROM), a rigid magnetic disk, and an optical disk. Current examples of optical disks include compact disk-read-only memory (CD-ROM), compact disk-read/write (CD-R/W), and DVD. A data processing system suitable for storing and/or executing program code will include at least one processor coupled directly or indirectly to memory elements through a system bus. The memory elements can include local memory employed during the actual execution of the program code, bulk storage, Subscriber Identity Module (SIM) card, and cache memories which provide temporary storage of at least some program code in order to reduce the number of times code must be retrieved from bulk storage during execution. Input/output (I/O) devices (including but not limited to keyboards, displays, pointing devices, remote controls, camera, microphone, temperature sensor, accelerometer, gyroscope, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem, and Ethernet cards are just a few of the currently available types of network adapters.

The foregoing examples and illustrative implementations of various embodiments have been provided merely for explanation and are in no way to be construed as limiting the embodiments disclosed herein. While the embodiments have been described with reference to various illustrative implementations, drawings, and techniques, it is understood that the words, which have been used herein, are words of description and illustration, rather than words of limitation. Furthermore, although the embodiments have been described herein with reference to particular means, materials, techniques, and implementations, the embodiments herein are not intended to be limited to the particulars disclosed herein; rather, the embodiments extend to all functionally equivalent structures, methods, and uses, such as are within the scope of the appended claims.

What is claimed is:

1. A processor-implemented method of joining two or more research studies to extract analytical insights for enabling cross-study analysis, the method comprising:
   identifying, using an identification module, at least one matched variable in a statistically representative sample in each of the two or more research studies;
   establishing, using a segment establishing module, for each combination of matched variables, a schema of segments, from the two or more research studies; and
   creating a joint study, using a joint study creation module, by combining responses from each of the two or more research studies within each segment of the statistically representative schema of segments,
   wherein a step of creating the joint study, in turn, comprises:
   determining a combination of matched variable segments associated with the highest number of variables, that have statistically representative samples based on a predetermined confidence level;
   receiving a user-selected variable to import and determine one or more variables that are related with each other and establish terms of relationship between the one or more variables; and
   changing outliers and unexpected values to be within a predetermined range and delete erroneous data, for combining responses from each of the two or more research studies within each segment of the statistically representative schema of segments.

2. The processor-implemented method of claim 1, wherein a step of creating the joint study comprises:
   determining a combination of matched variable segments associated with the highest number of variables, that have statistically representative samples based on a predetermined confidence level; and
   evaluating each variable combination that is also statistically representative of the population for combining responses from each of the two or more research studies within each segment of the statistically representative schema of segments.

3. The processor-implemented method of claim 1, wherein a step of establishing the schema of segments comprises:
   creating a list of schemas from each of the two or more research studies;
   running through each schema from the list of schemas and defining one or more segments in data sets corresponding to the two or more research studies;
   determining if each segment passes a predetermined statistical testing; and recommending schema based on the result of the predetermined statistical testing for each of the data sets.

4. The processor-implemented method of claim 3, wherein a step of recommending the schema comprises:
selecting schema that at least one of:
   a) passes a sample size test for each of the data sets;
   b) comprises a longest combination of matched variables in the schema; and
   c) that comprises a highest percentage of segments that passed a p-value test;
      wherein upon two schemas having same percentage of segments, an average p-value test is taken and the segment with a highest average p-value is selected.

5. The processor-implemented method of claim 1, wherein the one or more matched variable segments have one or more common traits and behavioral attributes.

6. The processor-implemented method of claim 1, wherein identifying one or more matched variables comprises:
classifying a plurality of variables by name;
implementing a meta-tagging from a wish list;
matching variables that are similar;
providing one or more suggestions of matched variables for selection by a user based on one or more pre-populated lists;
receiving a confirmation of the selection by the user;
determining if values between the variables can be matched among the matched variables;
determining variables that are similar using fuzzy matching; and
receiving matching of one or more remaining values from the user.

7. A system for joining two or more research studies to extract analytical insights for enabling cross-study analysis, the said system comprising:
a memory that stores non-transitory executable instructions and one or more executable modules;
a processor that executes the one or more executable modules for joining two or more research studies to extract analytical insights for enabling cross-study analysis, the one or more executable modules comprising:
   an identification module configured to identify at least one matched variable in a statistically representative sample of the two or more research studies;
   a segment establishing module configured to establish for each combination of matched variables, a schema of segments, from the two or more research studies and determine if each of the established schema of segments is statistically representative; and
a joint study creation module configured for creating a joint study by combining responses from each of the two or more research studies within each segment of the statistically representative schema of segments, wherein creating the joint study, in turn, comprises:
   determining a combination of matched variable segments associated with the highest number of variables, that have statistically representative samples based on a predetermined confidence level;
   receiving a user-selected variable to import and determine one or more variables that are related with each other and establish terms of relationship between the one or more variables; and
   changing outliers and unexpected values to be within a predetermined range and delete erroneous data, for combining responses from each of the two or more research studies within each segment of the statistically representative schema of segments.

8. The system of claim 7, wherein the segment establishing module is further configured for:
creating a list of schemas from each of the two or more research studies;
running through each schema and defining all segments in data sets corresponding to the two or more research studies;
determining if each segment passes a predetermined statistical testing; and
recommending schema based on the result of the predetermined statistical testing for each of the data sets.

9. The system of claim 8, wherein the segment establishing module is further configured for:
selecting schema that at least one of:
   a) passes a sample size test for each of the data sets;
   b) comprises a longest combination of matched vars in the schema; and
   c) that comprises highest percentage of segments that passed a p-value test;
   wherein upon two schemas having same percentage of segments, an average p-value test is taken and the segment with a highest average p-value is selected.

10. The system of claim 7, wherein the one or more matched variable segments have one or more common traits and behavioral attributes.

11. The system of claim 7, wherein the identification module is further configured for:
classifying a plurality of variables by name;
implementing a meta-tagging from a wish list;
matching variables that are similar;
providing one or more suggestions of matched variables for selection by a user based on one or more pre-populated lists;
receiving a confirmation of the selection by the user;
determining if values between the variables can be matched among the matched variables;
determining variables that are similar using fuzzy matching; and
receiving matching of one or more remaining values from the user.

12. One or more non-transitory computer-readable storage mediums storing one or more sequences of instructions, which, when executed by one or more processors, causes a method of joining two or more research studies to extract analytical insights for enabling cross-study analysis, the method comprising the steps of:
identifying, using an identification module, at least one matched variable in a statistically representative sample in each of the two or more research studies;
establishing, using a segment establishing module, for each combination of matched variables, a schema of segments, from the two or more research studies;
determining, using the segment establishing module if each of the established schema of segments is statistically representative; and
creating a joint study, using a joint study creation module, by combining responses from each of the two or more research studies within each segment of the statistically representative schema of segments, wherein a step of creating the joint study, in turn, comprises:
   determining a combination of matched variable segments associated with the highest number of variables, that have statistically representative samples based on a predetermined confidence level;

receiving a user-selected variable to import and determine one or more variables that are related with each other and establish terms of relationship between the one or more variables; and changing outliers and unexpected values to be within a predetermined range and delete erroneous data, for combining responses from each of the two or more research studies within each segment of the statistically representative schema of segments.

\* \* \* \* \*